(12) United States Patent
Herrmann et al.

(10) Patent No.: US 8,008,928 B2
(45) Date of Patent: Aug. 30, 2011

(54) APPARATUS AND METHOD FOR THE MEASUREMENT OF MASS AND/OR MOISTURE OF DIELECTRIC OBJECTS

(75) Inventors: Rainer Herrmann, Hamburg (DE); Udo Schlemm, Hamburg (DE)

(73) Assignee: TEWS Elektronik, Hamburg (DE)

( * ) Notice: Subject to any disclaimer, the term of this patent is extended or adjusted under 35 U.S.C. 154(b) by 445 days.

(21) Appl. No.: 12/145,711

(22) Filed: Jun. 25, 2008

(65) Prior Publication Data

US 2009/0009189 A1  Jan. 8, 2009

(30) Foreign Application Priority Data

Jun. 28, 2007  (DE) .......................... 10 2007 029 908

(51) Int. Cl.
*G01R 27/04*  (2006.01)
(52) U.S. Cl. ........................ 324/634; 324/636
(58) Field of Classification Search ........... 324/633–636
See application file for complete search history.

(56) References Cited

U.S. PATENT DOCUMENTS

| | | | | |
|---|---|---|---|---|
| 3,458,808 A * | 7/1969 | Agdur | .......................... | 324/633 |
| 4,257,001 A | 3/1981 | Partain et al. | | |
| 4,270,083 A * | 5/1981 | Fitzky et al. | .................. | 324/636 |
| 4,904,928 A * | 2/1990 | Lewis | ........................... | 324/636 |
| 5,124,662 A | 6/1992 | Downing et al. | | |
| 5,397,993 A | 3/1995 | Tews | | |
| 5,554,935 A * | 9/1996 | Kraszewski et al. | .......... | 324/633 |
| 5,648,038 A * | 7/1997 | Fathi et al. | .................... | 324/636 |
| 5,666,061 A * | 9/1997 | Assenheim | ................... | 324/636 |
| 5,736,864 A * | 4/1998 | Moller | .......................... | 324/633 |
| 5,977,780 A * | 11/1999 | Herrmann | ..................... | 324/636 |
| 6,476,619 B1 * | 11/2002 | Moshe et al. | ................. | 324/634 |
| 6,496,018 B1 * | 12/2002 | Nagata et al. | ................. | 324/636 |
| 6,897,659 B2 * | 5/2005 | Herrmann et al. | ............ | 324/633 |
| 6,922,061 B2 * | 7/2005 | Herrmann et al. | ............ | 324/633 |
| 7,042,231 B2 * | 5/2006 | Trebbi | .......................... | 324/639 |
| 2004/0225454 A1 * | 11/2004 | Herrmann et al. | .............. | 702/23 |

(Continued)

FOREIGN PATENT DOCUMENTS

DE  101 63 199 A1  3/2003

(Continued)

OTHER PUBLICATIONS

"Density-Indepent Moisture Metering in Fibrous Materials Using a Double-Cutoff Gunn Oscillator" by W. Hoppe, W. Meyer and W. Schilz (XP-002461926), 1980, pp. 1449-1452.

(Continued)

*Primary Examiner* — Timothy J Dole
(74) *Attorney, Agent, or Firm* — Vidas, Arrett & Steinkraus

(57) ABSTRACT

An apparatus for the measurement of mass and/or moisture of dielectric objects, with an analysing unit, at least one high frequency generator, at least one high frequency detector and with a high frequency resonator, wherein the at least one high frequency generator can generate at least two modes which are independent from each other, having different resonance frequencies in the resonator, the at least one high frequency detector can measure the occurring frequencies for each mode in the resonator, and the analysing unit can determine a shift of the resonance frequency (A) and a change of the resonance curve for the measured frequencies in each mode, and can calculate the mass and/or moisture of the dielectric object from the determined values for the shift of the resonance frequency (A) and the change of the resonance curve.

15 Claims, 4 Drawing Sheets

U.S. PATENT DOCUMENTS

2007/0018657 A1* 1/2007 Nagata et al. .............. 324/636

FOREIGN PATENT DOCUMENTS

| DE | 102 26 845 A1 | 8/2004 |
|---|---|---|
| EP | 0 287 725 A1 | 4/1987 |
| EP | 0 372 992 A2 | 8/1989 |
| EP | 0665426 | 8/1995 |
| EP | 1 467 191 B1 | 4/2003 |
| EP | 1 669 755 B1 | 8/2004 |
| WO | 97/01088 | 1/1997 |

OTHER PUBLICATIONS

"The Control and Ultilization of Dual Orthogonal Modes in a Rectangular Cavity", by Weigan Lin and Zhiqing Zhang, (XP-002498914), pp. 646-651.

"Design Aspects of Stripline Resonator Sensors for Industrial Applications" by M. Fischer, P. Vainikainen and E. Nyfors (XP-009069104), Journal of Microwave Power and Electromagnetic Energy, vol. 20, No. 4, 1995, pp. 246-257.

"Industrial Microwave Sensors" by Ebbe Nyfors and Pertti Vainikainen, (XP-002334964), 1989, pp. 1-350.

Linfeng Chen et al., "Cavity Perturbation Technique for the Measurement of Permittivity Tensor of Uniaxially Anisotropic Dielectrics" IEEE Transactions on Instrumentation and Measurement, vol. 48, No. 6, Dec. 1999; pp. 1023-1030.

Vepsäläinen et al., "Dielectric Anisotropy of Cellulose-Water Mixture Based on Microwave Resonator Method" Journal of Pulp and Paper Science: vol. 24 No. 6 Jun. 1998, pp. 188-196.

* cited by examiner

APPARATUS AND METHOD FOR THE MEASUREMENT OF MASS AND/OR MOISTURE OF DIELECTRIC OBJECTS

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The present invention is related to an apparatus and a method for the measurement of mass and/or moisture of dielectric objects.

With respect to the measurement of mass and/or moisture of dielectric objects, the present invention is based on the per se known microwave method, in which the object to be measured is put into a resonator. Due to its dielectric properties, the object changes an electromagnetic resonance impressed to the resonator. The mass and the moisture of the dielectric object is then determined from the change of the resonance curve and from the shift of the resonance frequency.

From EP 1 669 755 B1, the entire contents of which is incorporated herein by reference, a method for the measurement of the mass and/or moisture of the content of capsules is known. A measurement apparatus is provided for the measurement, which hast at least two resonators. The shift of the resonance frequency (A) and the broadening of the resonance curve (B) caused by the capsule are determined and analysed in both resonators. The first resonator has a measurement field which is homogeneous across the capsule extension, for determining the total mass and/or the moisture of the capsule. In the second resonator, in which the capsule is guided through a format-dependent sample guiding, the capsule content is not homogeneously distributed in the capsule due to the force of gravity, instead it is located in a part of the capsule by which a narrow measurement field for determining a location dependent profile of the mass and/or moisture is passed through. When the capsule format is changed, back fitting of the measurement arrangement with a new format dependent sample guiding is necessary.

From EP 1 467 191 B1, the entire contents of which is incorporated herein by reference, a method and an apparatus for determining the mass in portioned units of active ingredient is known. In the method, capsules, tablets or dragées are guided through a microwave resonator, which determines a shift of the resonance frequency and a broadening of the resonance curve. The measured variables serve for the determination of the mass with compensation of the moisture influence, wherein the mass is supposed to be directly proportional to the shift of the resonance frequency and directly proportional to the broadening of the resonance curve. However, it has come out that the results remain always affected by a certain degree of inaccuracy in certain applications.

From EP 0 372 992 A1, the entire contents of which is incorporated herein by reference, a measurement apparatus is known which has a spherical resonator. Into the resonator, two identical resonance modes are supplied, which have essentially the same resonance frequency, but different field orientations with respect to each other. The measurement assembly is intended for the determination of the mass of longitudinal filaments. The analysis of the results is based on the difference of the resonance frequency of the two modes. The difference of the resonance frequencies strongly depends on the mass as well as of the moisture, so that a measurement of the moisture not depending on the mass is not possible.

From U.S. Pat. No. 5,124,662, the entire contents of which is incorporated herein by reference, a method for classifying objects which are accommodated in a resonator is known. In the centre of the resonator, the objects to be classified are penetrated by an electric field which is as strong as possible. In order to be able to measure the sample in a way which does not depend on its location in the centre of the resonator, the microwave radiation of the different directions is superimposed, so that they differentiate to a field of maximal field strength in the centre of the resonator. In that the sample moves through the superposition of three orthogonal fields with about the same resonances, the shape and the orientation of the sample is averaged, and the result does not depend on the location of the sample. The information is achieved by the rotation of the electric field vector and it does not represent an independent analysis in different directions of space. In this classification method, it is disadvantageous that only spatial arithmetic means can be measured, and thus the measurement resolution is limited. Further it is disadvantageous that the method works properly only when the sample body is placed exactly into the resonator centre. For this purpose, an additional sensor arrangement is necessary.

From DE 102 26 845 A1, the entire contents of which is incorporated herein by reference, an arrangement for the determination of the distribution of the complex permittivity of an object to be observed is known. Microwaves of one single frequency are fed into the resonator, and the amplitude and the phase of the transmitted and reflected signals are analysed. There is no analysis of the resonance of the resonator. In the measurement, the object to be measured rests in the resonator, which has only the function of shielding. The spatial distribution of the permittivity is examined in that microwaves are coupled in and out at different positions.

The present invention is based on the objective to provide an apparatus and a method for the measurement of the mass and/or the moisture of dielectric objects which permits a rapid and accurate measurement on the dielectric objects.

BRIEF SUMMARY OF THE INVENTION

The apparatus according to the present invention serves for the measurement of the mass and/or the moisture of dielectric objects. The apparatus uses the microwave resonance method and it has an analysing unit, at least one high frequency generator, at least one high frequency detector and a high frequency resonator. The electromagnetic fields which generate the resonance are created via the at least one high frequency generator and are fed into the high frequency resonator. By the at least one high frequency detector, the electric and/or magnetic properties of resonances in the high frequency resonator can be measured. According to the present invention, the at least one high frequency resonator generates at least two modes in the high frequency resonator, which are independent from each other, having different resonance frequencies. In this context, independent modes means that when exciting the first mode, no excitation or only a small one is generated for the further modes, and the electric fields of the modes include an angle with each other which is different from 0° and 180°. The directions of the electric fields are not coincident, but oriented into different spatial directions which are independent from each other. Preferably, the fields stand vertically to each other. Further, the at least one high frequency detector can measure the occurring frequencies for each mode in the resonator. The high frequency detector is able to measure the occurring frequencies separately in each mode, wherein the measurement of the frequencies permits to determine a resonance curve and the resonance frequency. The analysing unit determines a shift of the resonance frequency and a change of the resonance curve for the measured frequencies of each mode. From the determined values for the shift of the resonance frequency and for the change of the resonance curve, the values for the mass and/or the moisture of the dielectric object in the resonator are determined independently from each other, in doing so the determined values are independent from the position, the way of movement and the special form of the object. A particular feature of the apparatus according to the present invention is that plural modes independent from each other are generated in one resonator and are analysed independently from each other. The present invention is based on the finding that the systematic variations of the measurement values which result in a known construction are due to the varying locations of the object to be measured. For instance, when looking at a dielectric object which has a different extension with respect to two axes and thus has different distributions of mass and moisture, the measurement result depends on the position of the object to be measured with respect to the electric field. By using two or more independent modes, the measurement process can be performed in directions of the object to be measured which are independent from each other, and therefore it can compensate for different spatial orientations of the sample during the movements and different sample shapes along the measured directions. Even a measurement with two independent modes achieves a significant improvement, compared with the one-mode measurement.

Further, the kind of the movement of the sample bodies through the measurement resonator plays only a minor role, so that a guiding which is depending on the format of the sample bodies is not absolutely necessary. With this, not only a time-consuming resetting of the apparatus upon format changes of the production procedure is avoided, but it is also possible to increase the throughput of sample bodies per time unit without a mechanical limitation. Through this, even at production rates up to $10^6$ sample bodies per hour, a 100% examination of the mass and of the moisture of every individual sample body is possible.

Preferably, at least two high frequency generators are provided, whose respective resonance frequencies are different from each other. Preferably, for each resonance mode with its resonance frequency, an own high frequency generator is provided.

In a preferred embodiment, the analysing unit determines a broadening of the resonance curve in the region of the resonance frequency as the change of the resonance curve. Alternatively, it is possible that the analysing unit determines the change of the resonance amplitude as the change of the resonance curve. It is also possible to use a combination of the change of the resonance amplitude and the broadening of the resonance curve for the analysis. For the analysis, the change of the resonance curve is combined with a shift of the resonance frequency by the entered dielectric object.

In one possible embodiment, the at least one high frequency detector can determine the frequencies occurring in the resonator several times during one measurement cycle. This means that during one measurement cycle, the change of the electromagnetic field is not measured only once, instead a plurality of measurement processes is performed during one measurement cycle.

As for the analysis of the measurement results for the different modes, there are different approaches. In one preferred approach, the analysing unit analyses the change of the resonance curve and the shift of the resonance frequency for each mode simultaneously. This means that the measurement results of all the three modes are analysed in one common point of time. In an alternative approach, the analysing unit analyses the change of the resonance curve and the shift of the resonance frequency for each mode independently. Both approaches for the analysis permit to obtain position-independent measurement results for the dielectric object.

In a preferred embodiment, each mode has a resonance frequency which is different from the resonance frequencies of the other modes. Preferably, in pairs at a time the resonance frequencies of the modes have a minimum frequency distance which amounts to preferably at least 100 MHz. Through the distance of the resonance frequencies of the individual modes it can be made sure that the signals for each resonance frequency can be analysed without disturbance by the signals of the other resonance frequencies. Thus, an independent analysis of the dielectric object is possible in each spatial direction which is preset by one of the modes, and averaging can be avoided.

In a preferred embodiment, exactly one high frequency generator and exactly one high frequency detector is provided for each mode. In an alternative embodiment, at least one of the high frequency generators is provided for the generation of plural modes. It is also possible to provide one high frequency detector, which can measure the occurring frequencies for plural modes. In a preferred embodiment, the high frequency detector and/or the high frequency generator can be switched over between the modes, so that a plurality of measurement values can be acquired during one measurement cycle.

In a preferred embodiment, a phase shifter is provided, which is associated with one of the high frequency generators in order to generate an electric field rotating in one plane. The rotation of the electric field is generated by the timed triggering of the phase shifter.

In the apparatus of the present invention, the resonator is purposefully dimensioned such that three modes are generated in the resonator. Preferably, in a central measurement region, the electric fields of the modes point into different spatial directions, which are purposefully linearly independent from each other, the spatial directions preferably standing vertically on each other. In addition, the threree modes are uncoupled. Thus, in the uncoupling devices belonging to one mode and leading to the respective detector, only modes are detected which belong to that mode, wherein other modes oscillating independently from it make no contribution to this measurement signal.

In an alternative embodiment, the high frequency resonator is executed as a cradle resonator with an upper resonator part and a lower resonator part. Between the upper resonator part and the lower resonator part, there is a gap for the dielectric object to be measured. In the realisation with a cradle resonator, preferably flat measurement targets with anisotropic material properties, like paper, Asiatic instant noodles (Yum Yum), wood boards and non-metallic materials rolled in one direction (like farinaceous products, for instance) are measured with respect to their moisture and density. In this, the flat measurement targets to be measured are supplied to the microwave measurement through the gap of the cradle resonator, wherein the measurement can take place at moved measurement target or at resting measurement target. In doing so, the material properties intended to be measured can be determined independently from the orientation of the measurement target in the resonator.

Preferably, two modes are generated in the cradle resonator, which reflect the flatness property of the critical targets. The electric field lines of the measurement field in the measurement gap are preferably oriented parallel to the planar extension of the measurement target. In the embodiment of the apparatus of the present invention, two different resonance modes are used, whose field lines are oriented vertically to each other and which run parallel to the planar extension of the measurement target at the same time.

In one preferred embodiment, the modes of the resonator are in a frequency range between 0.5 GHz and 20 GHz.

The geometric dimensions of the resonator, of the resonator interior in particular, can have different shapes. In a preferred embodiment, the resonator interior is formed as a cuboid. Alternatively, the resonator may also have an interior in the form of an ellipsoid or it may have a cylinder form with ellipse-like cross section.

In order to permit the supply of the dielectric objects into the measurement region of the resonator for measurement, the resonator is preferably provided with an entrance opening and an exit opening. The openings are preferably arranged in the resonator such that they permit a movement of the dielectric object to be measured through the resonator. In doing so, the movement may be a free movement, in which the object to be measured falls freely through the resonator under the influence of the gravity force, for instance. It is also possible to move the object to be measured freely through the resonator in an airflow.

In an extension of the present invention, a format piece for guiding the object to be measured is provided between the entrance opening and the exit opening. For instance, the object to be measured may freely slip or fall through the resonator along the format piece. This product-guiding, non-metallic, circular or rectangular pipe has a cross section diameter which is large enough that all the sample bodies in consideration can pass through it, thus, the format of the sample bodies does not play any role. However, in a preferred embodiment it is also possible to match the diameter of the sample pipe to the format of the sample bodies, in order to limit the movement possibilities of the sample bodies. In this case, when changing the format of the product, the format of the sample-guiding pipe has to be changed also. Particularly advantageous is to use format pieces when measuring with two independent modes.

The object according to the present invention is also resolved by a method for the measurement of mass and/or moisture of dielectric objects, one measurement being independent from the other. In the method of the present invention, there is provided an analysing unit, at least one high frequency generator and at least one high frequency detector, which co-operate with a resonator in order to acquire the change of a mode in the resonator. In the course of the measurement operation, at least two modes which are uncoupled from each other are generated in the resonator, and the occurring frequencies in the resonator are measured by the at least one high frequency detector for each one of the modes. The uncoupled modes are independent from each other and preferably, they form a measurement region in the resonator, in which the electric fields point into linearly independent spatial directions. The analysing unit analyses a shift of the resonance frequency for the measured frequencies of each mode, and it analyses a change of the resonance curve. From the shift of the resonance frequency and from the change of the resonance curve, the mass and/or the moisture of the dielectric object are determined independently from each other.

Preferably, the analysing unit analyses a broadening of the resonance curve as the change of the resonance curve.

In an alternative method, the analysing unit analyses a change of the resonance amplitude as the change of the resonance curve.

In a preferred embodiment of the method, the at least one high frequency detector determines the frequencies occurring in the resonator plural times in the course of one measurement cycle.

In the method of the present invention, each mode is preferably generated with a resonance frequency which is different from the resonance frequencies of the other modes. Preferably, the resonance frequencies of the modes have a minimal frequency distance pairwise at a time. The minimal frequency distance, which is for instance at least 100 MHz, makes sure that the resonance modes can be analysed individually and independently from each other. Thus, it is possible to acquire the dielectric properties of the objects to be measured for each direction of a mode independently from the directions of the other modes, so that an accurate analysis of the measurement results is possible and no averaging of the results has to be made.

In the analysis, the analysing unit analyses the change of the resonance frequency and the shift of the resonance frequency preferably simultaneously.

The demand to analyse simultaneously, which can be made for rapidly moving sample bodies, requires the independent use of three microwave generators and of three microwave detectors. When the movement of the sample body is slow enough, even the consecutive measurement of the resonance modes which are independent from each other may take place, by a switch of microwave generators and/or detectors to the different resonance modes.

In one preferred embodiment of the method, the change of the resonance curve and the shift of the resonance frequency are analysed for each mode in a point of time which is independent from the points in time in which the other modes are analysed. This is preferably made so when the movement of the product through the resonator takes place in a controlled manner, by using a format-depending guiding pipe.

Even with regard to the generation of the resonances in the resonator, different approaches are possible. In a first approach, each mode is generated by exactly one high frequency generator, and is measured by exactly one high frequency detector. Alternatively, it is also possible to generate at least two modes by one high frequency generator. Alternatively or as a supplement, it is also possible to measure the occurring frequencies in at least two modes by exactly one high frequency generator.

Preferably, one outcoupling device is provided for each mode, which is located in an oscillation node of the other modes. Purposefully, the resonance frequencies of the different modes are spaced apart by special constructional measures of the resonator, namely so far that the separation of the modes can be enhanced by special band pass filters in each individual detector line.

In an alternative embodiment of the method of the present invention, the at least one high frequency detector and/or the at least one high frequency generator is switched over between the modes.

In the method of the present invention, a phase shifter can also be used, in order to generate a rotating electric field in the resonator via two high frequency generators, in particular when the two resonance frequencies to be superimposed are very close in their frequencies, and thus, a common rotating resonance is possible. The measurement of the common resonance is then a superposition of the two original resonances.

Preferably, three modes are generated in the resonator. Preferably, the modes are oriented in the generator such that in one measurement region, the electric fields of the modes have different directions. Preferably, the electric fields stand in linearly independent directions in the measurement region and preferably they stand vertically to each other.

In the method of the present invention for the measurement of flat measurement targets in particular, a cradle resonator with an upper resonator part and a lower resonator part can be used, wherein a gap is provided between upper resonator part and lower resonator part, through which the dielectric object to be measured is guided. Thus, it is possible to arrange the dielectric object to be measured as resting in the gap or as being moved. In order to measure a flat measurement target with anisotropic material properties independently from its orientation in the resonator, the cradle resonator generates preferably two modes with different resonance frequencies.

In order to achieve a throughput of objects to be measured which is as great as possible, the same are moved through the resonator in the course of the measurement process. In doing so, it is possible that the objects move freely through the measurement region. For instance, a free movement may be generated by the force of gravity at objects falling freely or sliding on chutes, and/or by an air flow. In an alternative embodiment, the objects to be measured are guidedly moved through the measurement region. For instance, this means that the objects to be measured slide in format-depending chutes through the measurement region.

BRIEF DESCRIPTION OF THE SEVERAL VIEWS OF THE DRAWINGS

A preferred example of the realisation of the invention is explained in more detail in the following.

DETAILED DESCRIPTION OF THE INVENTION

Figure 1:
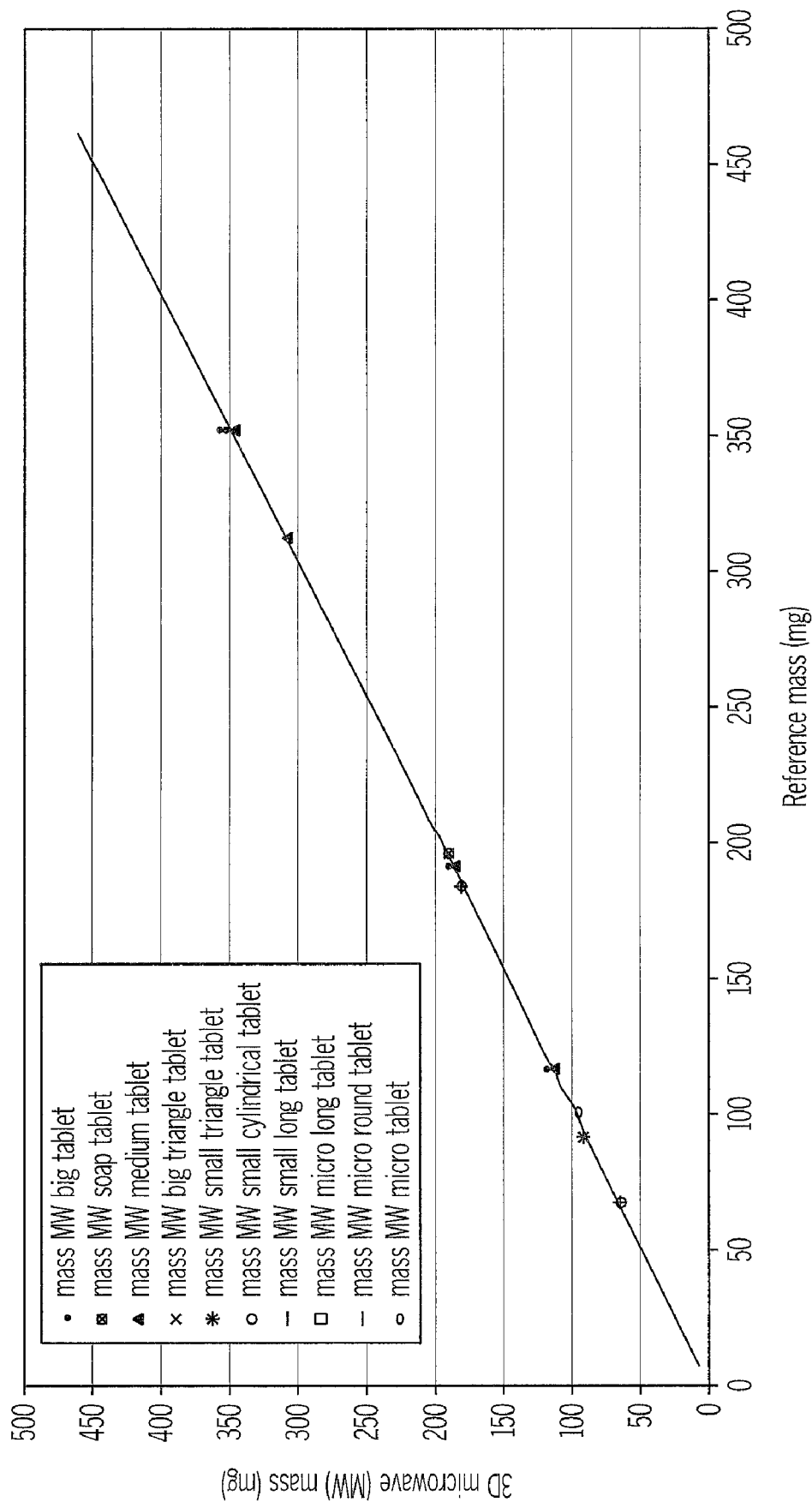
FIG. 1 shows measurement results for different sorts of tablets, which move through the microwave resonator on a chute with 40° inclination at uniform calibration of the measurement apparatus.

While this invention may be embodied in many different forms, there are described in detail herein a specific preferred embodiment of the invention. This description is an exemplification of the principles of the invention and is not intended to limit the invention to the particular embodiment illustrated A rapid and very accurate measurement of the mass of relatively small objects is particularly important in the field of pharmaceutical products, like tablets or capsules for instance, because in these objects, the overall mass is proportional to their content of active ingredient. Additional important information about the properties of these objects results from a measurement of the moisture, for instance, the mechanical properties of pressed tablets or hard gelatine capsules are strongly depending on their moisture content, and even the capsule content shows different properties when the moistures vary. A particular difficulty in the measurement of pressed tablets is that the same can have an arbitrary spatial shape. For instance, the objects to be measured can be shaped as to be spherical, cube-shaped, longitudinal, triangular or otherwise. With measurement targets which do not have spherical symmetry, the measurement in a resonator is always depending on the position. The result depends on the ratio of the surface portion of the object, which is parallel to the field lines of the resonator, to that surface portion of the object on which the field lines stand vertically. When the field lines and the surface portions of the measurement target are parallel, the electric field passes over into the product continuously, the detuning of the resonance frequency of the resonator results from the effect of the shortening of the wavelength in the interior of the product to be measured. In the lowering of the resonance frequency to the new value, the field has almost the identical spatial course as in the case of the void resonator. In this case, when the course of the field is not changed by the presence of a product, the solution of Maxwell's equation according to perturbation theory yields the following expression for the relative change of the resonance frequency:

$$\frac{f_0 - f_p}{f_0} = F(\varepsilon - 1)$$

wherein $f_o$ designates the resonance frequency of the void resonator, $f_p$ the resonance frequency which represents the effect of the parallel surface portions of the resonator filled with measurement target, F the ratio of the microwave field energy in the region of the sample to that of the complete resonator, and $\in$ the relative dielectricity constant (real part) of the sample material.

On the contrary, at field orientation vertical to the surface portion of the measurement object, the electric field jumps when it passes over into the sample material, namely about the factor to the value E/∈. When the resonance frequency which results from the effect of the vertical surface portions of the measurement object in the filled resonator is designated with $f_S$, the perturbation theory yields the following expression for the relative frequency shift at vertical field orientation:

$$\frac{f_0 - f_s}{f_0} = F\frac{\varepsilon - 1}{\varepsilon}$$

From the comparison of the two expressions, it becomes clear that an arbitrarily shaped measurement object, which is located in the microwave resonator, provokes different measurement signals depending on its orientation with respect to the microwave field in the measurement region. This is particularly important when moving objects are measured, which can pass through the measurement field in different orientations having equal volumes altogether, and thus can provoke different microwave measurement values. Through this results a limited exactness of the mass and/or moisture measurement. Even rolling or tumbling movement of the measurement objects when they pass through the measurement field leads to measurement errors.

In a preferred embodiment of the method of the present invention, for rapid mass and/or moisture measurement of arbitrarily shaped objects in arbitrary positions, it is worked with a microwave resonator using three simultaneously excitable resonance modes. The electric fields of these resonance modes stand vertical on each other in this example of realisation and form an orthogonal tripod. Thus, it is possible to acquire the respective volume portions of the measurement object in all the three spatial directions with the same orientation of the electric field.

Figure 3:
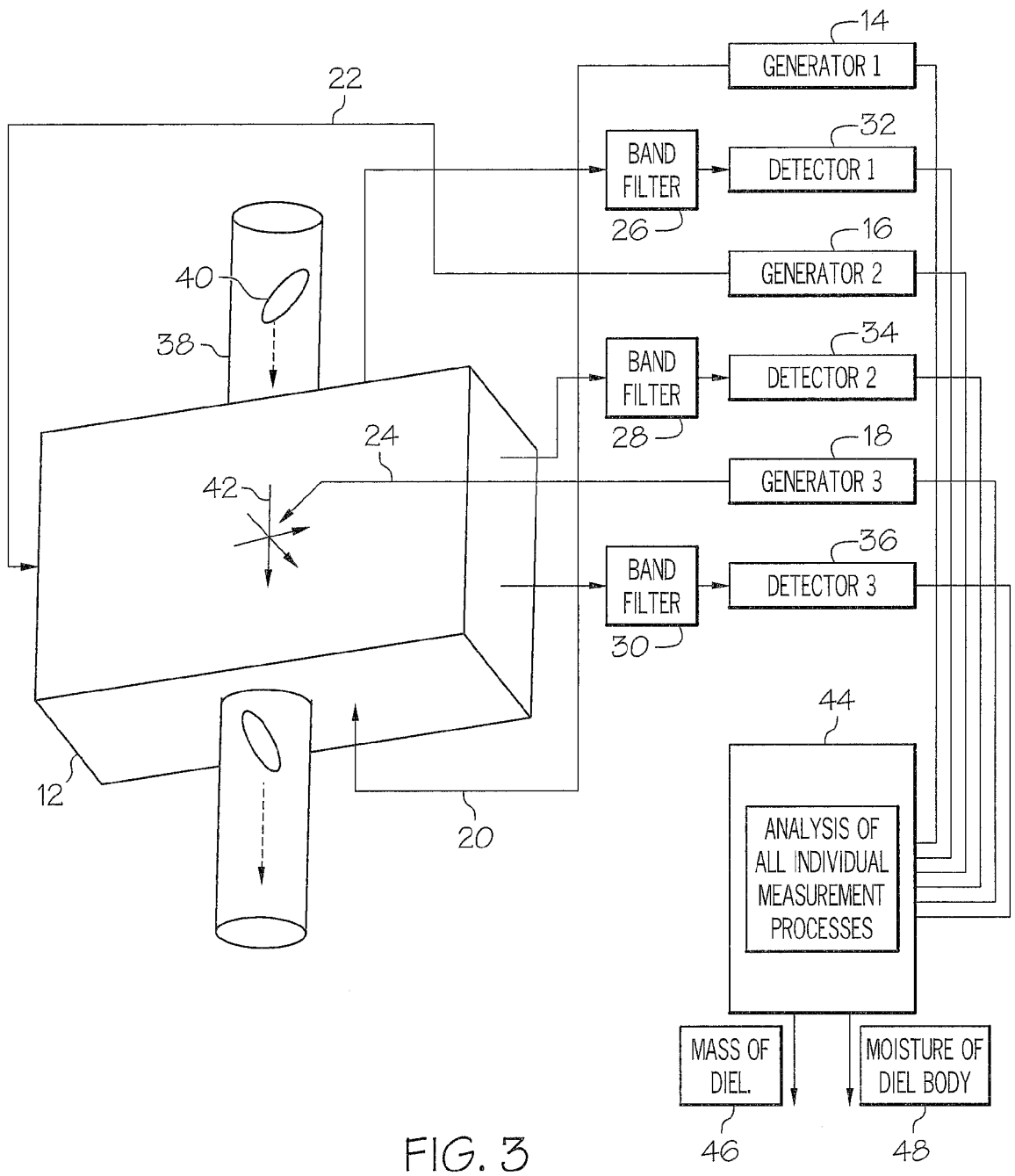
FIG. 3 shows a resonator with three independent resonance modes.

FIG. 3 shows in principle the measurement assembly of a resonator 12 with three independent resonance modes which stand vertically on each other. The resonance modes are generated by three high frequency generators 14, 16, 18 and are coupled in on different sides of the resonator 12. The coupling-in of the respective resonance modes is schematically represented by the arrows 20, 22 and 24. Also schematically shown by arrows is the line to band filters 26, 28, 30. As can be derived from the principle sketch in FIG. 3, the high frequency generator 16 feeds in its signal on a flat side of the resonator 12, which is coupled out at the opposite side and is forwarded to the band filter 28, from where the filtered results are sent to the detector 34. The same applies for the other spatial directions, wherein the generator 14 is coupled in on a flat side of the resonator 12 and the received signals are coupled out at the opposite side and are forwarded to the band filter 26. The filtered values reach the detector 32. For the third spatial direction an analogous process is performed, wherein here, the signals of the generator 18 are coupled in on the great flat side of the resonator 12 and are coupled out on the opposite great flat side, from where they are forwarded to the detector 36 via the band filter 30.

In FIG. 3, a guiding pipe 38 is also schematically represented, through which the tablets 40 to be measured can fall freely. The guiding pipe is made from a non-metallic material and passes through the centre of the resonator 12. As indicated in FIG. 3 by the tripod 42, the electric fields of the modes stand vertical on each other in the centre of the resonator 12. The functions of the band filters 26, 28, 30 are to filter the measured resonance values and to damp or respectively suppress undesired contributions to the resonances.

A condition for the use of band filters is of course that the three high frequency generators 14, 16, 18 work with resonance frequencies with are spaced apart from each other.

The data picked up by the detectors 32, 34, 36 are forwarded to an analysing unit 44. The analysing unit 44 is also connected to the generators 14, 16, 18 in order to trigger the same.

Then, the analysing unit 44 calculates the mass 46 of the dielectric body 6 and the moisture 48 of the dielectric body as a result. As the moisture, a concentration variable is always commonly understood, which results as a quotient of the mass of water and the overall mass (dry mass) of a sample body, indicated in percent.

A resonator with three simultaneously excitable resonance modes standing vertically to each other can be produced in different executions. One possible form of its realisation is a resonator which is shaped like an ellipsoid. A further possible form of its realisation is the shape of a cuboid. It is also possible to provide a resonator which has the form of a cylinder, whose cross sectional area has the form of an ellipse. In this, the coupling-in of the mode into the resonator takes place such that it is made sure for each of the three electric fields that only the desired resonance mode is excited. Further, it has to be made sure that there is no crosstalk between the individual modes, by which the measurement results would be adulterated. When there is crosstalk, the phenomenon occurs that by exciting one mode, other modes are also excited in addition, which contribute to the measurement result. On the one hand, such a crosstalk can be avoided by a particular arrangement of the field coupling-ins, by arranging the coupling antennas or coupling apertures of the excited resonance mode in the electric node of the other resonance modes. On the other hand, by constructional measures on the resonator, it can be taken care that the three resonance frequencies are spaced apart so far that by specially adapted band pass filters, the other modes can not cause any disturbances of the essential resonance mode.

In the preferred realisation example for the measurement method, the change of the resonance curve upon interaction with the measurement target is acquired in each resonance mode as a measurement value. Further, the shift of the resonance frequency (A) for each mode is acquired. As the change of the resonance curve, the broadening of the resonance curve (B) is measured in the realisation example. The measurement process as a whole yields three measurement values respectively, so that for each measurement object, the measurement values $A_1, A_2, A_3, B_1, B_2, B_3$ are at hand. These measurement values are depending on the moisture and the mass of the measurement object in the three spatial directions which are assigned to the resonance modes. From the six measurement values, the mass and the moisture of the whole measurement object can be calculated. The calculated values for mass and moisture are then independent from the orientation of the measurement object in the measurement field, and independent from the sample shape of the measurement object. At varying orientation of the measurement object in the measurement field, the signals in the individual spatial directions vary, yet the measured mass and the moisture of the entire measurement object remain uninfluenced by the orientation.

The calculation of the mass and of the moisture of the entire measurement object from the six individual measurement values is performed as follows:

$$\text{mass} = k_1 \cdot A_1 + k_2 \cdot A_2 + k_3 \cdot A_3 + k_4 \cdot B_1 + k_5 \cdot B_2 + k_6 \cdot B_3 + k_7$$

$$\text{moisture} = c_1 \cdot B_1/A_1 + c_2 \cdot B_2/A_2 + c_3 \cdot B_3/A_3 + c_4,$$

wherein the coefficients $k_j$ (j=1, ... 7) and $c_j$ (j=1 ... , 4) represent the calibration coefficients. The mass measurement is moisture-compensated; the moisture measurement thus obtained is also independent from the mass of the measurement object.

Taking into account that the measurement object needs a certain time in its movement through the measurement field, the six measurement variables can be recorded plural times in series in such a measurement cycle. In order to analyse the proper ones from this chronological series, there are in principle two different approaches. In the first approach, which is preferably used when an uncontrolled movement of the sample through the resonator is prevented or limited by format-depending sample guiding, the maximum of the shift of the resonance frequency is chosen for each sample, and the respective measurement values A and B are determined for this mode at this point in time. In an alternative analysing process, the maximum of the detuning of the resonance frequency when the measurement object passes through the resonator is determined for one mode. When the maximum of the detuning of the resonance frequency has been detected for one mode, the measurement values of the remaining modes are analysed at the same point in time. By doing so, it is attained that the measurement object is measured in a uniform position by the three modes standing orthogonal to each other. Thus, the sample body is observed from different sides in an arbitrary position, so that a complete compensation of the position influence is possible. This second analysing process can be used when sample bodies pass through the resonator in a random movement and any guiding is omitted in favour of a high throughput of sample bodies over time.

Figure 2:
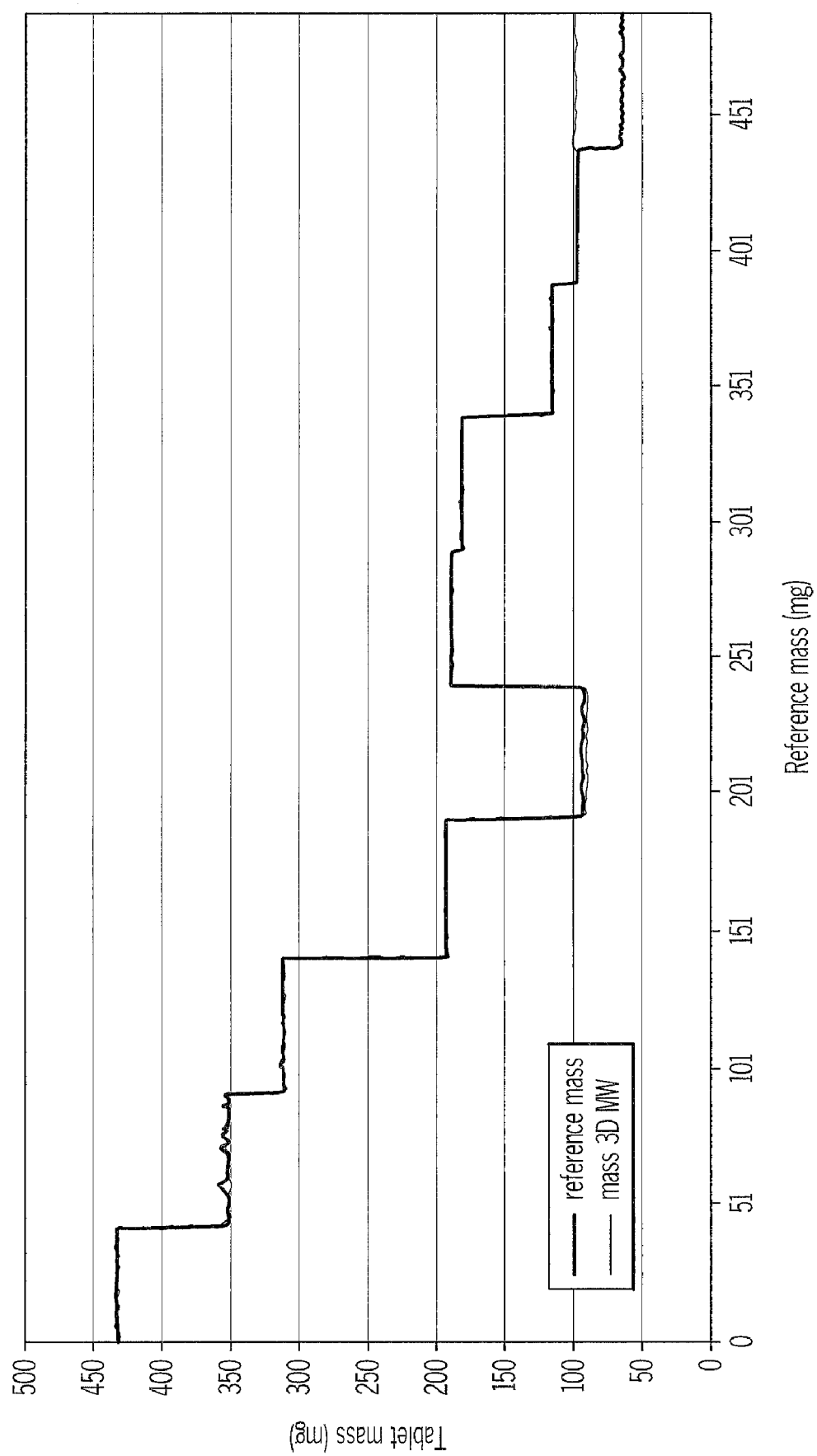
FIG. 2 shows measurement results for different tablets, which move through the resonator on a chute with 40° inclination, at uniform calibration of the measurement apparatus.

The transportation of the measurement objects through the resonator may take place through a non-metallic pipe, either falling freely or slidingly. For instance, FIG. 1 shows the measurement results with a chute inclined about 40°, on which a plurality of differently shaped tablets having different weights slide through the measurement field. In the measurement shown in FIG. 1, these tablets are plotted against their reference mass. The curve shows already very clearly that it is possible with such a three mode measurement method to increase the measurement precision for the mass measurement of the sample bodies significantly with one single calibration curve, independently from position variations of the sample bodies, from their shape, from their moisture content and their composition. This result is also confirmed by FIG. 2, in which 50 samples of tablets at a time with the same shape and mass have sledded through the measurement field of the resonator on a 40° chute. Even here it becomes clear that reliable measurements can be obtained in a mass range of 50 mg to 450 mg, without that systematic errors occur in the frame of the desired accuracy.

For measurements on very small measurement objects, the measurement precision of the mass detection can be increased further by using additional format pieces for guiding the measurement objects. In particular, this is the case when the three measurement fields used for measurement are not completely homogeneous in the measurement region. The homogeneity of the fields contributes strongly to the mass detection, but for the moisture detection it plays only a minor role. As the format pieces, sample tubes with different inner diameter adapted to the sample size can be used, for instance. Chutes of different ranges can also be used as the format pieces.

Besides to the measurement with three resonance modes contemplated above, it is also possible to realise the measurement method of the present invention by one single HF generator and one single HF detector only, wherein a fast switchover is performed during the measurement by a semiconductor switch. In this, it is important that the switchover speed is great in relation to the speed of the measurement object in the measurement region, so that it is possible to measure all the three modes at approximately equal position of the measurement object. The analysis of the measurement variables $A_i$, $B_i$ ($i=1, \ldots, 3$) can then take place as described above.

Figure 4:
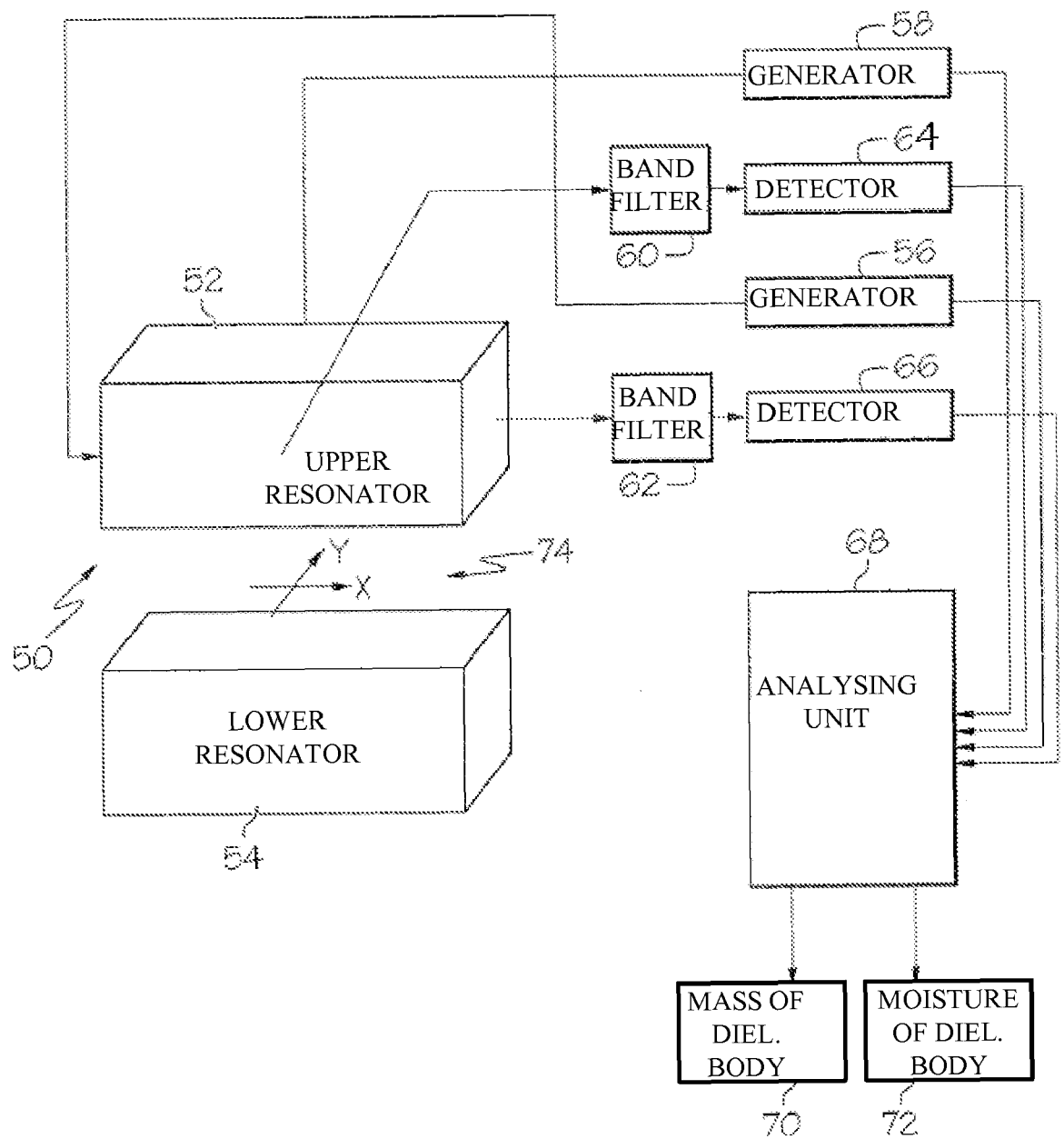
FIG. 4 shows a cradle resonator for the measurement of flat articles, in a schematic representation.

FIG. 4 shows a cradle resonator 50, consisting of an upper resonator part 52 and a lower resonator part 54. The upper resonator part 52 is fed with microwaves by the high frequency generators 56 and 58, and two linearly independent resonance modes with different resonance frequencies are generated. Via band filters 60 and 62, the resonances forming themselves in the upper resonator part are guided back to two of the detectors, namely 64 and 66. The generators 56, 58 and the detectors 64, 66 are connected to an analysing unit 68. The analysing unit analyses the changes which are formed in the resonance modes and outputs a mass 70 and a moisture 72 as a result. In these values of mass and moisture it is dealt with values which are related to one two-dimensional area.

For measurement, the flat material to be measured is guided through a resonator gap 74, which is formed between upper resonator part 52 and lower resonator part 54.

In the gap 74, the electric field lines of the resonance modes are arranged parallel to the two-dimensional extension of the measurement material in different directions.

The two resonance modes used by the cradle resonator 50 have field lines which are oriented vertically on each other and run parallel to the two-dimensional extension of the measurement material at the same time. An example for two of such directions is drawn in FIG. 4 by the two-dimensional coordinate system with its x and y axes.

In a preferred application, the cradle resonator has a gap width of about 5 to 40 mm.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. An apparatus for measuring mass and/or moisture of dielectric objects, the apparatus comprising:
   an analysing unit;
   at least two high frequency generators;
   at least two high frequency detectors; and
   a high frequency resonator,
   wherein the at least two high frequency generators simultaneously generate at least two modes that are independent from each other, each mode having a resonance frequency that is different from the resonance frequencies of the other modes, two neighboring frequencies having a minimum distance of 100 MHz, and the electric fields of each mode stand vertically to the electric fields of each other mode in a measurement region,
   wherein the at least two high frequency detectors measure the occurring frequencies for each mode in the resonator simultaneously, and
   wherein the analysing unit:
      determines a shift of the resonance frequency and a change of the resonance curve for the measured frequencies in each mode, and
      calculates the mass and/or moisture of the dielectric object from the determined values for the shift of the resonance frequency and the change of the resonance curve.

2. The apparatus of claim 1, wherein the analysing unit can determine a broadening of the resonance curve as the change of the resonance curve.

3. The apparatus of claim 1, wherein three modes can be generated in the resonator, and wherein the electric fields of the three modes are oriented in directions which are linearly independent from each other in one measurement region.

4. The apparatus of claim 1, wherein the high frequency generator is a cradle resonator having an upper resonator part and a lower resonator part, and wherein a gap for the dielectric object to be measured is formed between the upper resonator part and the lower resonator part, so that two modes are generated in the cradle resonator.

5. The apparatus of claim 4, wherein a flat shaped measurement target can be arranged in the gap or can be lead through the same as the dielectric object which is to be measured.

6. The apparatus of claim 1, wherein the modes of the resonator are in a frequency range between 0.5 GHz and 20 GHz.

7. The apparatus of claim 1, wherein the resonator has the form of a cuboid.

8. The apparatus of claim 1, wherein the resonator has the form of an ellipsoid.

9. The apparatus of claim 1, wherein the resonator has the form of a cylinder with an ellipse-shaped cross section.

10. The apparatus of claim 1, wherein the resonator has an entrance opening and an exit opening, which permit a movement of the dielectric object to be measured through the resonator.

11. The apparatus of claim 10, wherein a format piece for guiding the object to be measured through the resonator is provided between the entrance opening and the exit opening.

12. The apparatus of claim 1, wherein a coupling-out device is provided for each mode, which is located in an oscillation node of the other modes.

13. A method for measuring mass and/or moisture of dielectric objects, the method comprising:
   simultaneously generating at least two modes with a resonance frequency which is different from the resonance frequencies of the other modes wherein two neighboring frequencies have a minimum distance of 100 MHz, and the electric fields of each mode stand vertically to the electric fields of each other mode in a measurement region;
   measuring frequencies occurring in the resonator with at least two high frequency detectors for each mode simultaneously;
   analyzing a shift of the resonance frequency and a change of the resonance curve for the measured frequencies of each mode; and
   determining the mass and/or the moisture of the dielectric object based on the analysis.

14. The method of claim 13, further comprising:
   analyzing the broadening of the resonance curve as the change of the resonance curve.

15. The method according to claim 13, wherein three modes are generated in the resonator.

* * * * *